US006568447B1

(12) United States Patent
Sakai et al.

(10) Patent No.: US 6,568,447 B1
(45) Date of Patent: May 27, 2003

(54) COVER GLASS ADHERING DEVICE (75) Inventors: Takayoshi Sakai, Koushoku (JP);
Shinji Tokudaiji, Koushoku (JP);
Takashi Yoshiike, Koushoku (JP);
Kiyokazu Iijima, Koushoku (JP);
Seiichi Takizawa, Koushoku (JP)

(73) Assignees: Kabushiki Kaisha Tiyoda Seisakusho, Nagano (JP); Sakura Finetechnical Co., Ltd., Tokyo (JP)

( * ) Notice: Subject to any disclaimer, the term of this patent is extended or adjusted under 35 U.S.C. 154(b) by 0 days.

(21) Appl. No.: 09/565,656

(22) Filed: May 5, 2000

(30) Foreign Application Priority Data

May 11, 1999 (JP) ............................................. 11-130347

(51) Int. Cl.$^7$ .............................. G01N 1/28; G01N 1/31
(52) U.S. Cl. ........................ 156/356; 156/539; 156/556; 156/563; 156/573; 422/99; 118/677
(58) Field of Search ................................. 156/351, 356, 156/556, 563, 573, 578, 539; 221/33, 73; 422/99; 118/677, 679

(56) References Cited

U.S. PATENT DOCUMENTS

| 474,267 A | 5/1892 | Shimmer | |
|---|---|---|---|
| 4,428,793 A | 1/1984 | Sato et al. | |
| 4,537,648 A | * 8/1985 | Shiino et al. | 156/351 |
| 5,029,838 A | * 7/1991 | Kunihiro | 271/117 |
| 5,033,730 A | * 7/1991 | Davies et al. | 271/106 |
| 5,989,386 A | * 11/1999 | Elliott | 156/344 |
| 6,050,314 A | * 4/2000 | Kakishima | 156/356 |

FOREIGN PATENT DOCUMENTS

| EP | 0292285 | 11/1988 |
|---|---|---|
| JP | 58-30636 | 2/1983 |
| JP | 58040519 | 3/1983 |
| JP | 59157533 | 9/1984 |
| JP | 61066141 | 4/1986 |
| JP | 09-325105 | * 12/1997 |

* cited by examiner

*Primary Examiner*—Richard Crispino
*Assistant Examiner*—Sue A. Purvis
(74) *Attorney, Agent, or Firm*—Jordan and Hamburg LLP (57) ABSTRACT

The cover glass adhering device is capable of dropping fixed amount of mounting medium, using cover glasses having various length, and being small in size. In the cover glass adhering device, a drop nozzle drops the mounting medium onto a specimen on a slide glass, which is held horizontally. A removing member removes a drop of the mounting medium dangling from the drop nozzle. The removing member is located outside of the slide glass. A traveling unit travels the drop nozzle, from which the dangling drop of the mounting medium has been removed by the removing member, along the specimen on the slide glass so as to drop a prescribed amount of the mounting medium over the specimen.

26 Claims, 11 Drawing Sheets

COVER GLASS ADHERING DEVICE

BACKGROUND OF THE INVENTION

The present invention relates to a cover glass adhering device, more precisely relates to a cover glass adhering device, which mounts a cover glass onto a mounting medium covering a microscope specimen on a slide glass.

Figure 17:
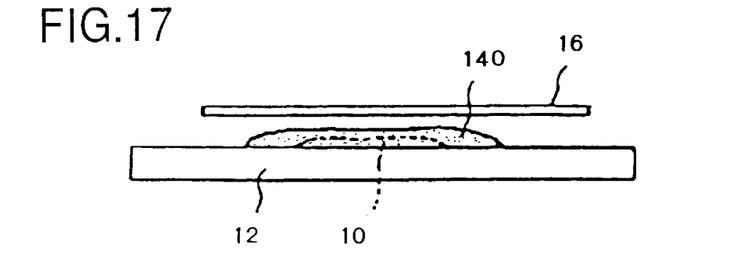
FIG. 17 is an explanation view showing how to make a microscope specimen.

A method of making a microscope specimen, e.g., a tissue slice of an affected part of a patient, is shown in FIG. 17. The method comprising the steps of: slicing a tissue of the affected part; mounting the tissue slice 10 onto a slide glass 12; removing fat from the tissue slice 10; dyeing the tissue slice 10; dropping a mounting medium, which includes a solvent, onto the tissue slice 10 on the slide glass 12; and mounting a cover glass 16 onto a mounting medium pattern 140, which is formed by dropping the mounting medium along the tissue slice 10. The solvent in the mounting medium evaporates, and the mounting medium solidifies, so that the cover glass 16 is adhered on the slide glass 12.

For example, in hospitals, a lot of microscope specimens must be made in a short time.

Figure 18:
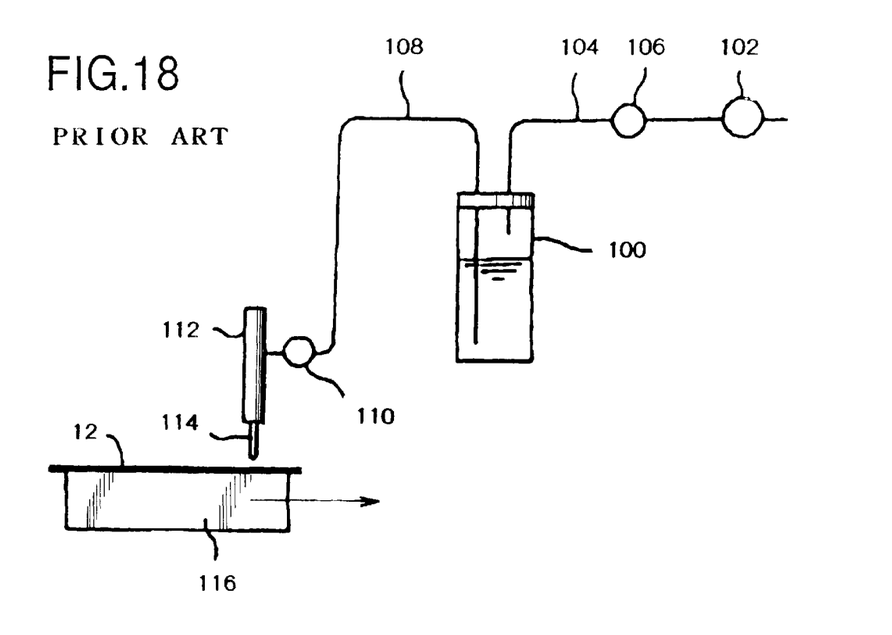
FIG. 18 is an explanation view of a conventional drop nozzle.

To automatically make the microscope specimens, a dropping device (see FIG. 18), which automatically drops the mounting medium onto the specimens 10 on the slide glasses 12, was disclosed in the Japanese Patent Gazettes No. 59-157533 and No. 61-66141. In FIG. 18, compressed air, which is compressed by a compressor 102, is introduced into an upper inner space of a container 100, in which the mounting medium including the solvent is reservoired, via a regulator 106 of a pressurizing pipe 104. The mounting medium in the container 100 is pushed and sent, by the compressed air in the container 100, to a tank 112 via a spouting pipe 108, whose one end is opened in a lower part of the container 100. The mounting medium in the tank 112 is dropped onto the specimen on the slide glass 12 from a drop nozzle 114. Amount of dropping the mounting medium can be controlled by a control valve 110, which opens and closes with regular time separations. A table 116, on which the slide glass 12 is mounted, is slid in a direction of an arrow, so that the mounting medium can be dropped along the specimen 10 and the mounting medium pattern 140 having the prescribed pattern can be formed.

Usually, a plurality of cover glasses 16, each of which will cover the specimen 10 on the slide glass 12, are piled in a holder container. Thus, the uppermost glass 16 of the piled cover glasses must be taken out from the holder container.

The cover glass 16 has a thickness of 0.06–0.25 mm and flat surfaces, so the piled cover glasses 16 are mutually tightly fitted.

A device for taking out the uppermost cover glass of the piled cover glasses 16 from a holder container was disclosed in the Japanese Patent Gazette No. 58-30636. The device is shown in FIG. 19.

Figure 19:
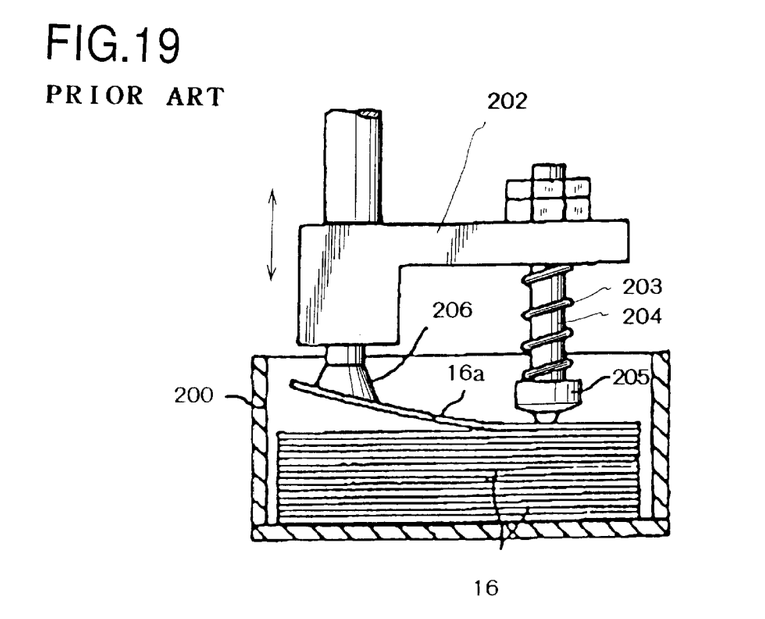
FIG. 19 is an explanation view of conventional means for taking out the cover glass.

In the device shown in FIG. 19, a press member 204 is pierced through an elevating member 202, which can be moved in the vertical direction, and its lower end 205 is biased downward by a spring 203. A sucking pad 206 is provided to the elevating member 202. To take out the uppermost cover glass 16a of the piled cover glasses 16 in a holder container 200, the elevating member 202 is moved downward to push one end of the uppermost glass 16a by the lower end 205 of the press member 204, and the other end of the uppermost glass 16a is pulled upward by the sucking member 206 of the elevating member 202. At that time, an upper end of the press member 204 is projected upward, against the elasticity of the spring 203, from the elevating member 202.

Next, the elevating member 202 is moved upward as shown in FIG. 19. With this action, the other end of the cover glass 16a is pulled upward by the sucking member 206, and the cover glass 16a is bent downward, so that the cover glass 16a can be removed from the piled glasses 16 and taken out from the holder container 200.

A device for mounting and adhering the cover glass 16, which has been taken out from the holder container 200, onto the mounting medium pattern 140, which has been formed on the slide glass 12 by dropping the mounting medium, was disclosed in the Japanese Patent Gazette No. 3-40367. The device is shown in FIG. 20.

Figure 20:
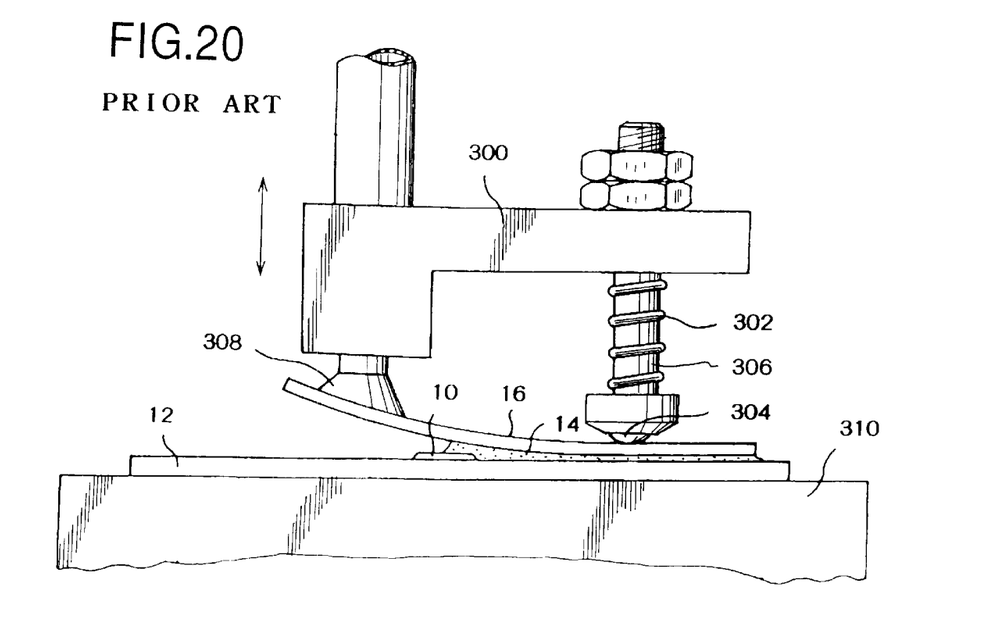
FIG. 20 is an explanation view of conventional means for mounting the cover glass.

In the device shown in FIG. 20, a press member 306 is pierced through a holder member 300, which can be moved in the vertical direction, and its lower end 304 is biased downward by a spring 302. A sucking pad 308 is provided to the holder member 300. To mount and adhere the cover glass 16 onto the mounting medium pattern 140, which includes the specimen 10 and which is formed on the slide glass 12 by dropping the mounting medium, one end of the cover glass 16 is sucked by the sucking pad 308. At that time, the other end of the cover glass 16 is pushed downward by the lower end 304 of the press member 306, so that the other end of the cover glass 16 is located below the one end thereof.

Next, the holder member 300 is moved downward and toward the slide glass 12, which has been horizontally mounted on a table 310, until the other end of the cover glass 16 contacts an upper face of one end of the slide glass 12. With further moving the holder member 300 downward, the one end of the cover glass 16 is gradually moved toward the upper face of the slide glass 12. With this action, the cover glass 16 pushes the mounting medium pattern 140 toward the other end of the slide glass 12 and tightly fits thereon, so that air bubbles between the slide glass 12 and the cover glass 16 can be pushed out by the cover glass 16.

Upon completing or immediately before completing the action of mounting the cover glass 16, the sucking pad 308 releases the cover glass 16 and the holder member 300 is moved upward, so that the cover glass 12 can be left on the slide glass 12.

The inventors of the present invention have studied a cover glass adhering device, which includes a unit for taking out the cover glass and a unit for mounting the cover glass, so as to automatically make a microscope specimen.

In the cover glass adhering device, the sequential steps for adhering the cover glass onto a specimen on a slide glass can be executed automatically.

However, the cover glass adhering device has following disadvantages: it is difficult to always drop fixed amount of mounting medium onto the specimen; it is difficult to always form a mounting medium pattern into a prescribed pattern; the device must be large in size; and a long cover glass cannot be used.

SUMMARY OF THE INVENTION

An object of the present invention is to provide a cover glass adhering device, which is capable of dropping fixed amount of mounting medium, using cover glasses having various length, and being small in size.

The inventors have studied and found: the size of the device can be smaller than that of the conventional device, in which the slide glass is slid, by sliding a drop nozzle; and fixed amount of the mounting medium can be supplied by using a proper supply unit for supplying fixed amount of the mounting medium, e.g., a plunger pump, and removing a drop of the mounting medium dangling from said drop nozzle.

And, they found that mounting medium patterns can be always formed into a prescribed pattern by the steps of: stopping a movement of the drop nozzle at a position, at which the drop action of the mounting medium is begun; beginning the drop action thereof; and moving the drop nozzle along the slide glass.

Further, they found that a rotational angle of a holding member, which holds one end of the uppermost cover glass of a plurality of cover glasses, can be made narrower by slantingly piling the cover glasses in a holder container.

The cover glass adhering device of the present invention, which mounts a cover glass onto a mounting medium covering a microscope specimen on a slide glass, comprises:
  a drop nozzle for dropping the mounting medium onto the specimen on a slide glass, which is held horizontally;
  a removing member for removing a drop of the mounting medium dangling from the drop nozzle, the removing member being located outside of the slide glass; and
  a traveling unit for traveling the drop nozzle, from which the dangling drop of the mounting medium has been removed by the removing member, along the specimen on the slide glass so as to drop a prescribed amount of the mounting medium over the specimen.

Another cover glass adhering device of the present invention, which mounts a cover glass onto a mounting medium covering a microscope specimen on a slide glass, comprises:
  a holding member being capable of holding one end of an uppermost glass of the cover glasses, which have been slantingly piled in a holder container;
  a rotary unit for turning the holding member so as to downwardly bend the uppermost glass and remove the same from the adjacent cover glass; and
  a vertical drive unit for vertically moving the holding member and the rotary unit.

Further, the cover glass adhering device of the present invention, comprises:
  means for conveying a slide glass, the conveying means being provided between a basket container, in which a plurality of slide glasses, on each of which a microscope specimen is mounted, are accommodated, and a rack, in which the slide glasses, on each of which a cover glass is mounted to cover the specimen, will be accommodated, the conveying means having a conveyor plate, which intermittently conveys the slide glass, which is horizontally held, toward the rack;
  means for taking out the slide glass from the basket container and horizontally putting the slide glass onto a predetermined position in the conveyor plate;
  means for dropping a mounting medium, the dropping means including:
    a drop nozzle dropping the mounting medium onto the specimen on the slide glass, which has been horizontally conveyed to a predetermined position by the conveying means;
    a traveling unit for traveling the drop nozzle along the specimen on the slide glass so as to drop a prescribed amount of the mounting medium supplied by a supply unit, which is capable of supplying the prescribe amount of the mounting medium, over the specimen; and
    a control section for controlling the traveling unit and the supply unit so as to stop the movement of the drop nozzle at a start end, at which the drop nozzle starts to drop the mounting medium onto the slide glass and move the drop nozzle along the slide glass after starting the drop action; and
  means for holding and adhering the cover glass, the holding-and-adhering means including:
    a holding member being capable of holding one end of an uppermost glass of the cover glasses, which have been slantingly piled in a holder container;
    a take-out unit turning the holding member so as to downwardly bend the uppermost glass and remove the same from the adjacent cover glass, then taking out the uppermost glass from the holder container; and
    a mounting unit gradually mounting the cover glass, whose one end is held by the holding member, onto the mounting medium, which covers the specimen on the slide glass conveyed to a predetermined position, from the other end to the one end.

In the cover glass adhering device, the traveling unit may include:
  an elevating unit for moving the drop nozzle in the vertical direction; and
  a sliding unit for sliding the drop nozzle along the specimen on the slide glass until a position outside of the slide glass. With this structure, the drop nozzle can be smoothly moved to the position out of the slide glass.

The cover glass adhering device may further comprise a container, in which a solvent for preventing solidification of the mounting medium is reservoired, being located at a position, which is outside of the slide glass and at which a front end of the drop nozzle can enter the container. With this structure, closing the drop nozzle can be prevented even if the device is stopped for a long time.

In the cover glass adhering device, the control section of the dropping means may control the movement of the traveling unit so as to put the front end of the drop nozzle into a container, in which a solvent for preventing solidification of the mounting medium is reservoired, before dropping the mounting medium, while stopping or after the dropping action. With this structure, closing the drop nozzle can be prevented even if the device is stopped for a long time.

In the cover glass adhering device, the holding-and-adhering means may comprise:
  a sucking member being capable of sucking the one end of the uppermost glass of the cover glasses, which have been slantingly piled in the holder container;
  a rotary unit for turning the sucking member so as to make the other end of the uppermost glass contact with an inner face of the holder container and bend the uppermost glass; and
  a pin being provided in the vicinity of the sucking member, the pin downwardly pushing the uppermost glass, which is bent, so as to deform the uppermost cover glass into an S-shape. With this structure, long cover glasses can be easily taken out from the holder container.

In the cover glass adhering device, the control section of the dropping means may control the traveling unit and the supply unit so as to stop the travel of the drop nozzle, which is moved along the slide glass, after stopping the drop action. With this structure, no air bubbles are left in the mounting medium when the cover glass is mounted on the slide glass.

In the cover glass adhering device, a supporting section of the rack, in which the slide glasses are accommodated, may have a inclined face, with which side faces of the slide glasses come into contact. With this structure, the mounting medium stuck on the side faces of the piled slide glasses will not be stuck on the rear faces thereof.

BRIEF DESCRIPTION OF THE DRAWINGS

Embodiments of the present invention will now be described by way of examples and with reference to the accompanying drawings, in which.

DETAILED DESCRIPTION OF THE PREFERRED EMBODIMENTS

Preferred embodiments of the present invention will now be described in detail with reference to the accompanying drawings.

Figure 1:
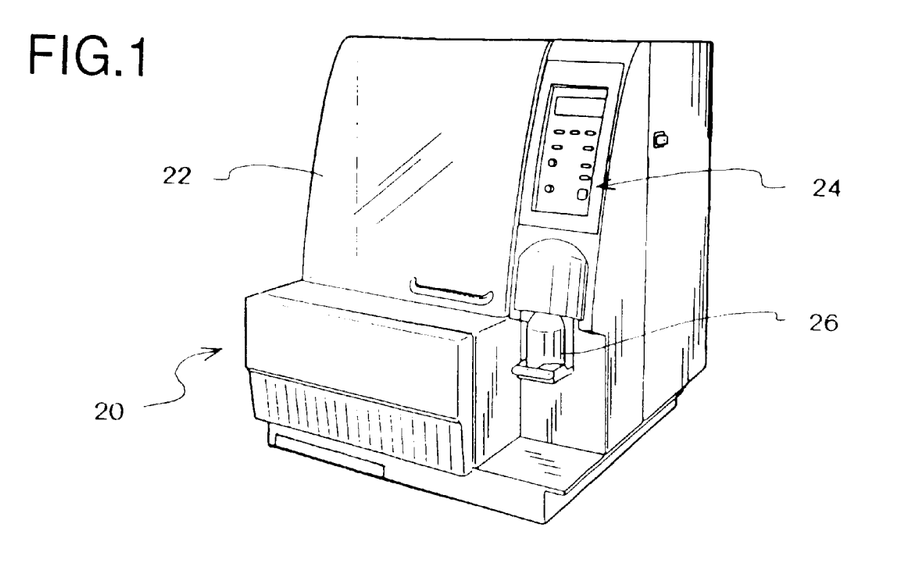
FIG. 1 is a perspective view of a cover glass adhering device of an embodiment of the present invention.
Figure 2:
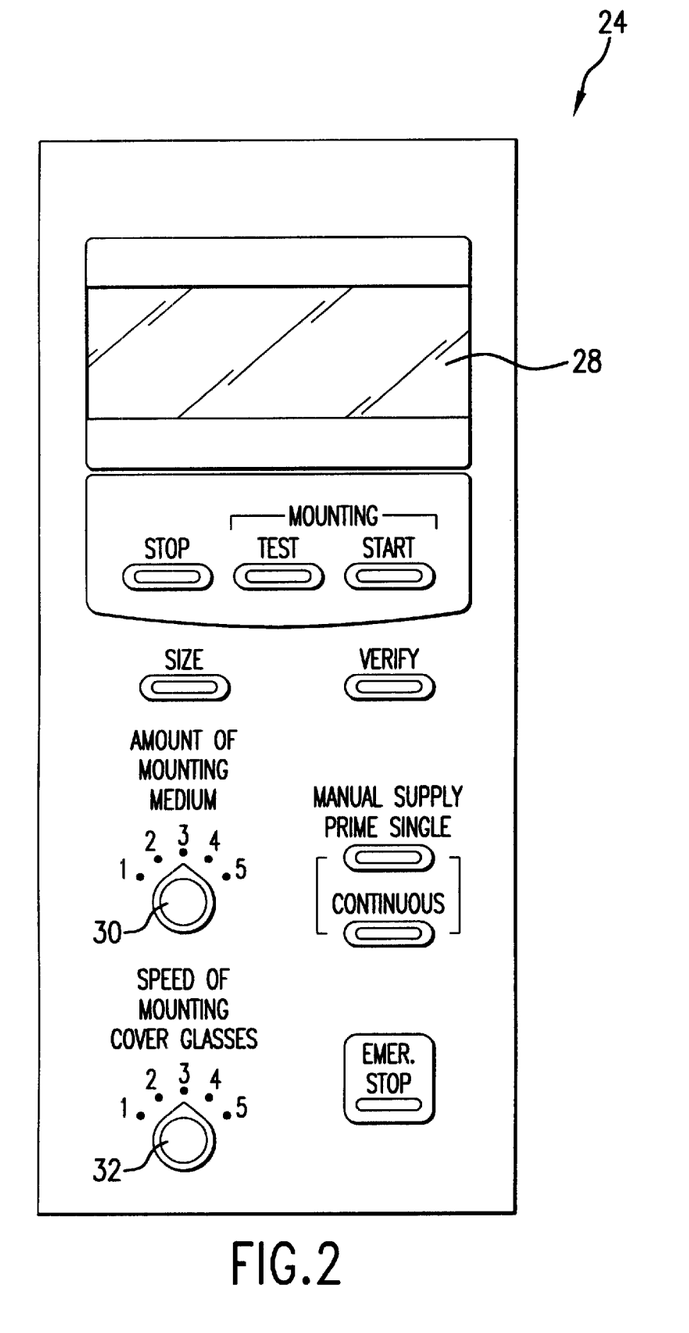
FIG. 2 is a front view of an operation panel of the device shown in FIG. 1.

The cover glass adhering device of the present embodiment of the present invention is shown in FIG. 1. The cover glass adhering device has a transparent cover 22 for opening and closing a body section 20, and the body section 20 has an operating panel 24. Further, a container 26, in which mounting medium is reservoired, is inserted in the body section 20. As shown in FIG. 2, a screen 28, on which operating conditions are shown, start and stop buttons for each operation, a check button, etc. are provided in the operating panel 24. An adjusting dial 30 for adjusting amount of supplying the mounting medium and a speed adjusting dial 32 for adjusting speed of mounting the cover glasses are also provided in the operating panel 24.

Figure 3:
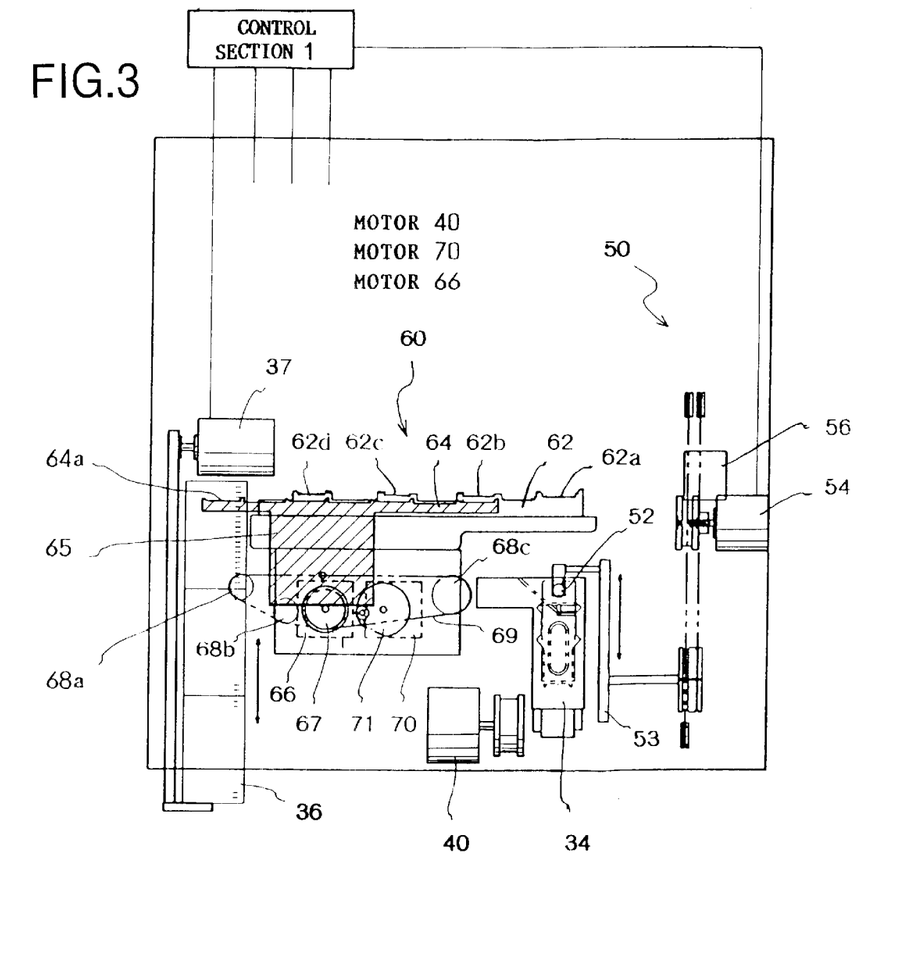
FIG. 3 is an explanation view of the device shown in FIG. 1.

As shown in FIG. 3, a basket container 34, in which a plurality of slide glasses on each of which a specimen is mounted are accommodated, and racks 36, which store the slide glasses on each of which the cover glass is adhered, are provided in the body section 20 shown in FIG. 1.

Figure 4:
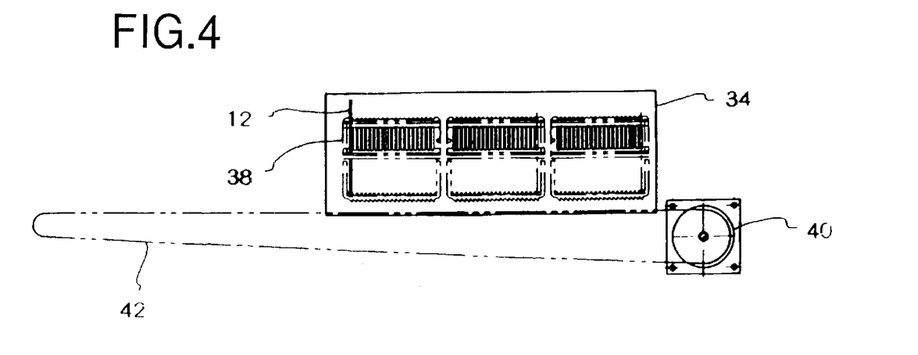
FIG. 4 is an explanation view of a basket container shown in FIG. 3.
Figure 5:
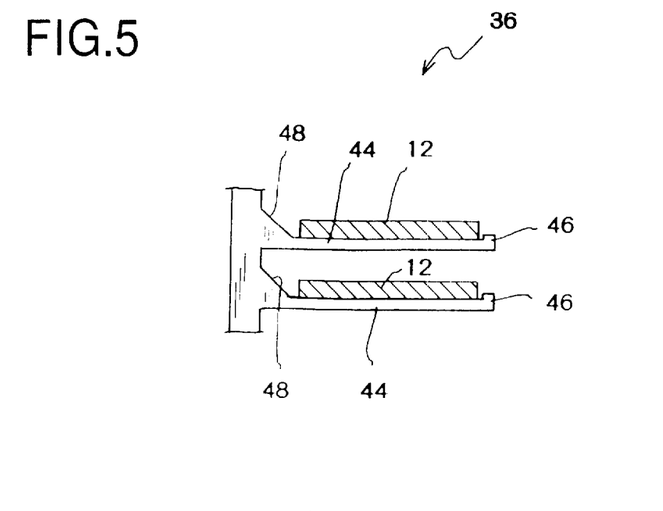
FIG. 5 is a partial sectional view of a rack shown in FIG. 3.

As shown in FIG. 4, a plurality of baskets 38, in each of which a plurality of the slide glasses on which the specimens are mounted are vertically stored, are provided in the basket container 34. The basket container 34 can be moved by a wire 42, which is driven by a motor 40. The racks 36 are capable of moving in the vertical direction, by a motor 37, so as to store the slide glasses in order. As shown in FIG. 5, supporting sections 44, which support both ends of the slide glasses 12, are formed in slide glass accommodating sections of the racks 36. Front ends 46 of the supporting sections 44 are formed into an L-shape so as to prevent the slide glasses 12 from falling down. Further, inner parts 48 of the supporting sections 44 are slopes. With the slopes, even if side faces of the slide glasses 12, which have been mounted on the supporting sections 44, contact the inner parts 48, the mounting medium stuck on the side faces of the slide glasses 12 will not be sent to the rear faces of the slide glasses 12 via gaps between the side faces of the slide glasses 12 and the inner parts 48 of the supporting sections 44.

A conveying means 60, which intermittently conveys the slide glasses 12, which is taken from the basket 38 by slide glass take-out means 50, to the racks 36, is provided between the basket container 34 and the racks 36.

Figure 6:
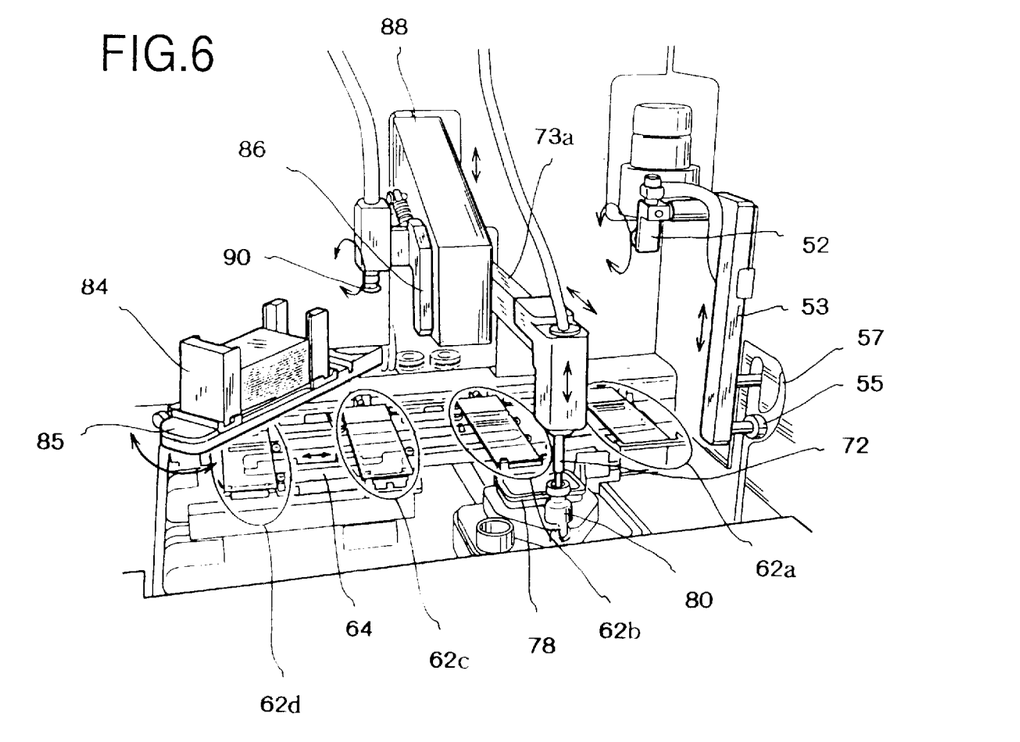
FIG. 6 is a partial perspective view of the device shown in FIG. 1.

The slide glass take-out means 50 includes: a motor 54 for vertically moving a member 53, to which a sucking pad 52 for sucking one end of the slide glass 12, which has been vertically stored in the basket 38, is fixed; and a weight 56. As shown in FIG. 6, a guide rod 55, which is guided by a guide groove 57 formed in an inner face of the body section 20, is provided to the member 53 so as to rotate the sucking pad 52. The sucking pad 52 is rotated so as to horizontally arrange the slide glass 12, whose one end has been sucked by the sucking pad 52 and vertically pulled upward.

Note that, the sucking pad 52 is connected to one end of a hose whose the other end is connected to vacuum means.

The slide glass 12, which has been horizontally arranged, is located in the vicinity of the take-out means 50, then mounted onto a recessed first station 62a of a supporting member 62, which is capable of supporting both ends of the slide glass 12. In the supporting member 62, a recessed second station 62b, a recessed third station 62c and a recessed fourth station 62d are further formed, toward the racks 36, with regular separations.

The slide glass 12 which is horizontally mounted on the first station 62a is conveyed to the second station 62b, the third station 62c and the fourth station 62d, in order, by a conveying plate 64 of the conveying means 60. A plurality of recesses 64a are formed in an upper face of the conveying plate 64 and arranged from the take-out means 50 side to the racks 36 side. A projected section 65 is downwardly projected from a bottom face of the conveying plate 64. The projected section 65 is connected to a belt 69, which is engaged with a pulley 67, which is directly driven by a motor 66, and free pulleys 68a, 68b and 68c. The projected section 65 is vertically moved by a cam 71, which is driven by a motor 70. With this structure, the conveying plate 64 is moved upward at a predetermined position and horizontally moved in a predetermined direction, then the conveying plate 64 is moved downward at a predetermined position and horizontally moved in the reverse direction.

As shown in FIG. 3, the motors 37, 40, 54, 66 and 70 are controlled by a control section 1. By the control section 1, the slide glass 12, which has been horizontally mounted on the first station 62a by the take-out means 50, is moved to a position above the supporting member 62 by the conveying plate 64, and the slide glass 12 is horizontally conveyed, in the same state, to a position above the second station 62a, then the slide glass 12 is moved downward, by the conveying plate 64, so that the slide glass 12 can be horizontally mounted on the second station 62b. The conveying plate 64, which has been moved downward, is horizontally moved toward the first station 62a so as to convey the next slide glass 12. As described above, the slide glass 12 can be conveyed to the rest stations and stored in the racks 36 in order.

As shown in FIG. 6, the second station 62b is located in the vicinity of a drop nozzle 72 for dropping the mounting medium; the third station 62c is located in the vicinity of a sucking pad 90 for sucking the cover glass.

Figure 7:
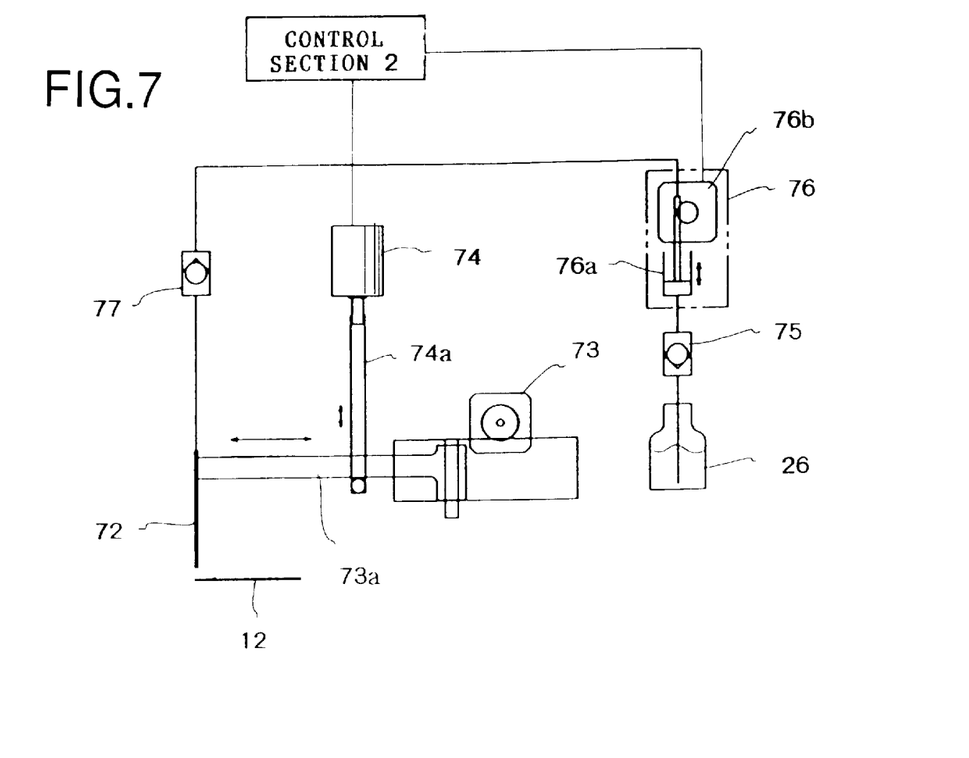
FIG. 7 is an explanation view of means for dropping mounting medium of the device shown in FIG. 1.

As shown in FIG. 7, means for dropping the mounting medium includes: the drop nozzle 72; a connecting member 73a, whose one end is connected to the drop nozzle 72; a motor 73, which constitutes a slide unit for horizontally sliding the drop nozzle 72 and which is connected to the other end of the connecting member 73a; and a solenoid 74, which constitutes an elevating unit for vertically moving the drop nozzle 72 and whose rod 74a is connected to a mid part of the connecting member 73a. The motor 73 and the solenoid 74 are controlled by a control section 2. The control section 2 moves the drop nozzle 72 in the horizontal direction and the vertical direction. A plunger pump 76, which is an example of a supply unit for supplying fixed amount of the mounting medium, supplies the mounting medium from the container 26 to the drop nozzle 72. A motor 76b for moving a plunger 76a of the plunger pump 76 is also controlled by the control section 2.

The drop nozzle 72 is capable of dropping the mounting medium onto the slide glass 12, which has been horizontally arranged, by horizontally moving in the longitudinal direction of the slide glass 12. The plunger pump 76 is capable of always supplying the fixed amount of the mounting medium.

Figure 8:
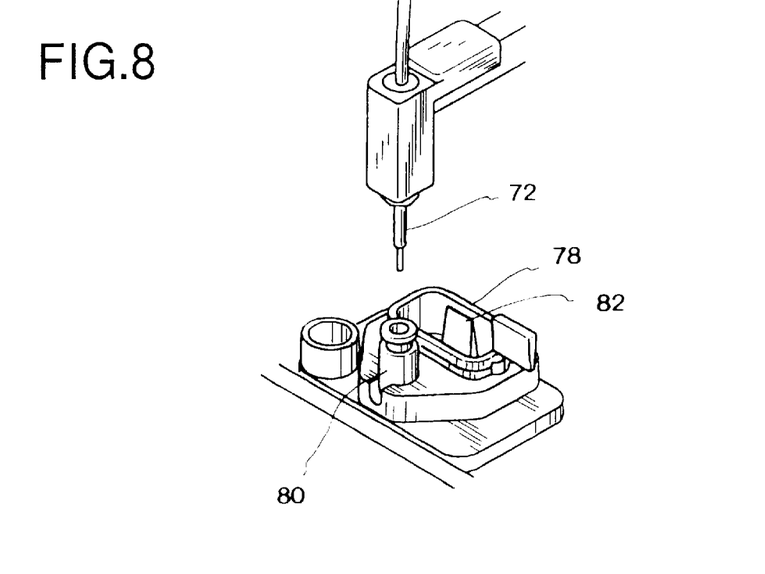
FIG. 8 is a partial perspective view of the dropping means of the device shown in FIG. 1.
Figure 9:
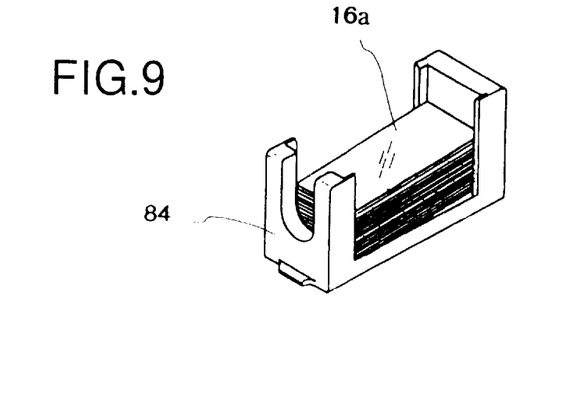
FIG. 9 is a perspective view of a holder container.

The drop nozzle 72 shown in FIG. 6 is capable of horizontally moving to a position outside of the slide glass 12. A discharge tray 78 and a container 80, in which a solvent for preventing solidification of the mounting medium is reservoired, are located at positions, which are outside of the slide glass 12 and within a moving range of the drop nozzle 72. As shown in FIG. 8, a removing member 82, which is capable of removing a drop of the mounting medium dangling from the drop nozzle 72, is vertically extended from the discharge tray 78.

Check valves 75 and 77, which are capable of preventing reverse flow of the mounting medium, are provided to mid positions of a tube between the container 26 and the drop nozzle 72.

As shown in FIG. 6, a sucking pad 90 for sucking the cover glass and a holder container 84, in which a plurality of cover glasses 16 are piled, are provided in the vicinity of the third station 62c. The holder container 84 is mounted on a container table 85, which is capable of horizontally rotating. The cover glasses 16 are slantingly piled in the holder container 84. The uppermost cover glass 16a is taken out from the holder container 84 by the sucking pad 90, which acts as a holding member.

Figure 10:
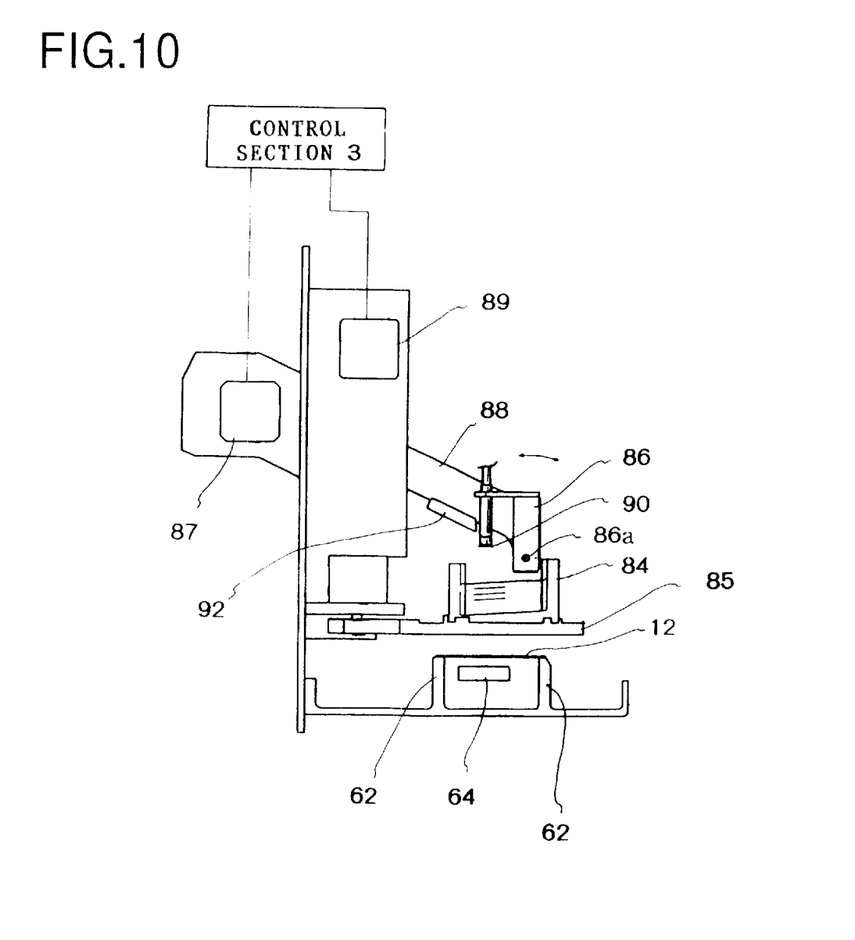
FIG. 10 is an explanation view of means for holding and adhering the cover glass of the device shown in FIG. 1.

The sucking pad 90 constitutes means for holding and adhering the cover glass 16 (see FIG. 10). The holding-and-adhering means further includes: an arm 86 in which the sucking pad 90 is provided to one end; a motor 87 for rotating the arm 86 about an axis 86a; and a motor 89 for vertically moving an arm member 88, to which the arm 86 is attached. Further, the arm member 88 has a pin 92, which is provided in the vicinity of the sucking pad 90. The motors 87 and 89 are controlled by a control section 3.

Note that, the sucking pad 90 is connected to one end of a hose whose the other end is connected to the vacuum means.

By the dropping means shown in FIGS. 7 and 8, the slide glass 12, which is horizontally located on the first station 62a, is conveyed to the second station 62b by the conveying plate 64 so as to drop the mounting medium onto a specimen on the slide glass 12. This action is controlled by the control section 2, which controls the solenoid 74 and the motors 73 and 76b.

The action of the dropping means shown in FIGS. 7 and 8 will be explained with reference to FIGS. 11A–11C.

Figure 11A:
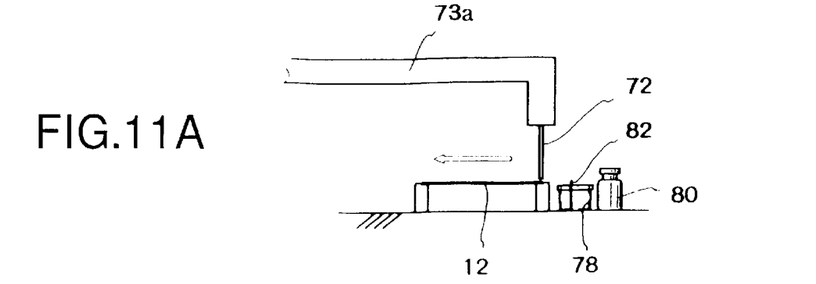
FIGS. 11A–C are explanation views showing a series of action of the dropping means.
Figure 11B:
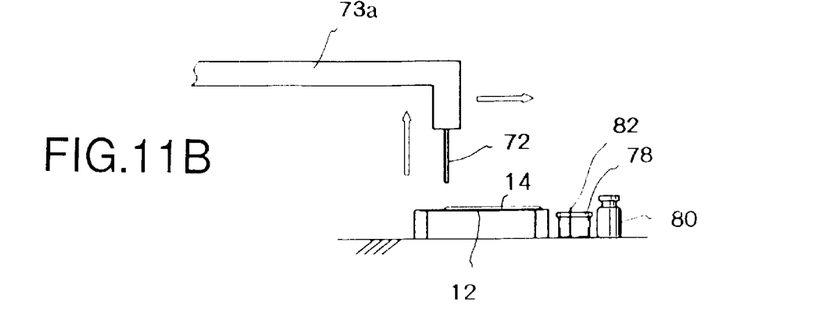

The drop nozzle 72 drops the mounting medium onto the specimen on the slide glass 12 and is moved, in the longitudinal direction of the slide glass 12, away from the discharge tray 78, which is located outside of the slide glass, by the motor 73, which is provided to the other end of the connecting member 73a whose one end is connected to the drop nozzle 72, and the solenoid 74, which is connected to the mid part of the connecting member 73a (see FIG. 11A). When the drop nozzle 72 reaches a predetermined position on the slide glass 12, supplying the mounting medium by the plunger pump 76 and the travel of the drop nozzle 72 in the longitudinal direction of the slide glass 12 are stopped. Then the drop nozzle 72 are moved upward and moved toward the discharge tray 78 (FIG. 11B). When the drop nozzle 72 reaches the discharge tray 78, the drop nozzle 72 is moved downward again and moved away from the discharge tray 78 (see FIG. 11C).

Figure 11C:
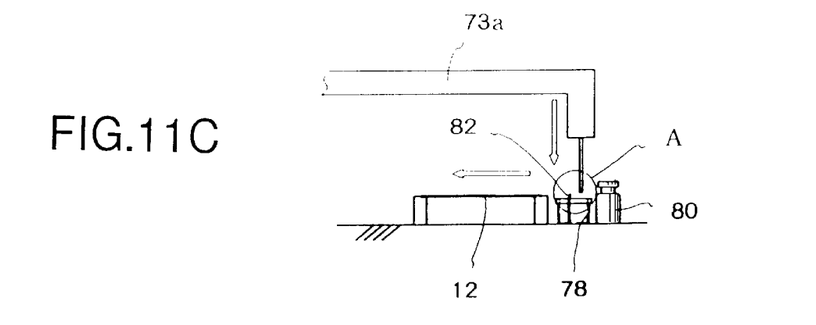
Figure 12:
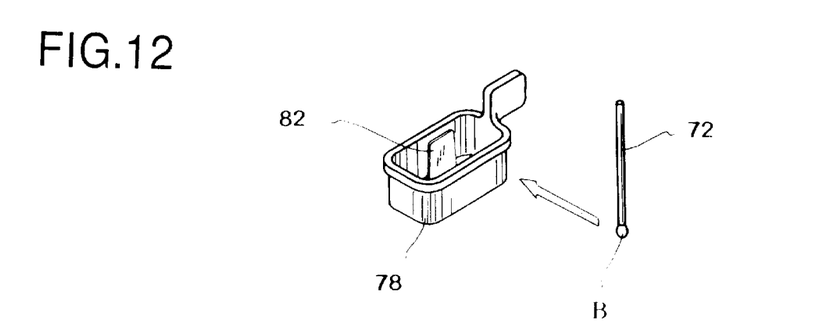
FIG. 12 is an enlarged view of a part "A" showing in FIG. 11C.

As shown in FIG. 12, which is an enlarged view of a part "A" of FIG. 11C, a drop "B" of the mounting medium, which is reservoired in the drop nozzle 72, is apt to dangle from a lower end of the drop nozzle 72, which has been stopped. If the drop nozzle 72, which holds the drop "B", restarts to drop the mounting medium, amount of the mounting medium dropped on the slide glasses 12 are varied. To drop fixed amount of the mounting medium, the lower end of the drop nozzle 72 is passed over the removing member 82, which is vertically extended from the discharge tray 78, so as to make the drop "B" contact the removing member 82 and remove the drop "B" from the drop nozzle 72.

After removing the drop "B", the drop nozzle 72 restarts to drop the mounting medium at a predetermined position on the slide glass 12, so that the fixed amount of the mounting medium can be dropped onto the slide glass 12.

Amount of supplying the mounting medium can be adjusted by the adjusting dial 30 of the operating panel 24 (see FIG. 2).

In FIGS. 11A–11C and 12, the drop "B" of the mounting medium is removed from the lower end of the drop nozzle 72, and the drop action of the drop nozzle 72 is started when the drop nozzle 72 reaches the predetermined position on the slide glass 12. On the other hand, the drop action of the drop nozzle 72 and the travel of the drop nozzle 72, in the longitudinal direction of the slide glass 12, are stopped when the drop nozzle 72 reaches another predetermined position on the slide glass 12. Then the drop nozzle 72 is moved upward.

Figure 13A:
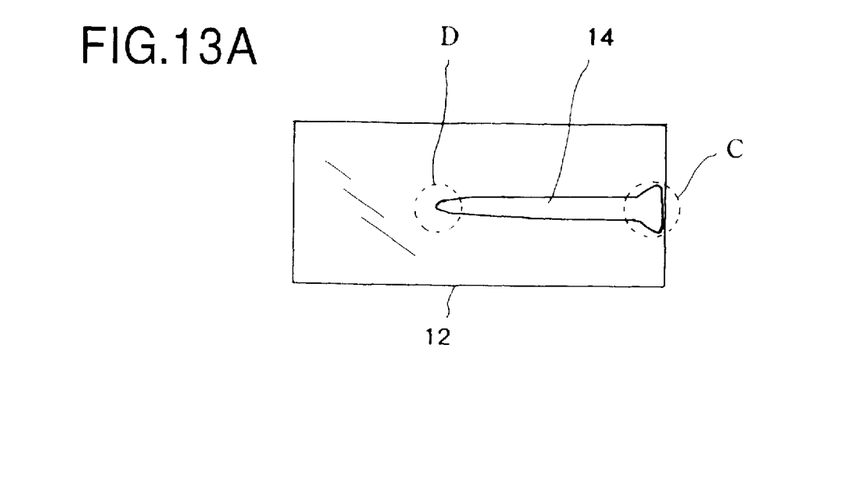
FIGS. 13A and 13B are plan views of a mounting medium pattern, which is formed by the steps shown in FIGS. 11A–11C.
Figure 13B:
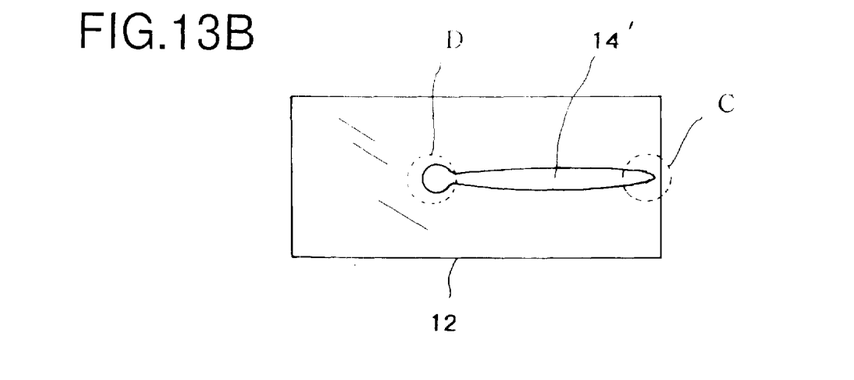

With the drop action and the travel of the drop nozzle 72, a mounting medium pattern 14' shown in FIG. 13B is sometimes formed. A start end "C" of the pattern 14', at which the drop action is started, is narrow; A stop end "D" of the pattern 14', at which the drop action is stopped, is formed like a wide bump. With the pattern shape shown in FIG. 13B, air is apt to invade into a space between the cover glass 16 and the slide glass 12 when the cover glass 16 is mounted onto the pattern 14'.

By starting and stopping the drop action and the travel of the drop nozzle 72 simultaneously, the pattern 14' is formed. Namely, at the start end "C", the mounting medium is begun to be dropped and traveled simultaneously, so that the shape of the start end "C" is formed narrower.

On the other hand, at the stop end "D", the drop action and the travel of the mounting medium is stopped simultaneously, so that the final drop of the mounting medium falls onto the stop end "D" and the shape thereof is formed like a circular wide bump.

To avoid forming the mounting medium pattern 14' shown in FIG. 13B, the control section 2 controls the solenoid 74 and the motor 73, which move the drop nozzle 72 in the predetermined direction, and the motor 76b, which drives the plunger pump 76 for sending the mounting medium to the drop nozzle 72, so as to execute the steps of: once stopping the travel of the drop nozzle 72 at the start end, at which the mounting medium is begun to be dropped onto the slide glass 12; beginning to drop the mounting medium; and starting to travel the drop nozzle 72 along the surface of the slide glass 12. With this action, the start end "C" of the mounting medium pattern can be wide as shown in FIG. 13A.

On the other hand, the control section 2 controls the solenoid 74 and the motors 73 and 76b so as to stop the travel of the drop nozzle 72 after the drop action is stopped. With this action, the stop end "D" of the mounting medium pattern can be narrower as shown in FIG. 13A.

With the shape of the mounting medium pattern 14 shown in FIG. 13A, air is not apt to invade in the space between the cover glass 16 and the slide glass 12 when the cover glass 16 is mounted onto the pattern 14 from the start end "C".

The slide glass 12, on which the mounting medium is dropped at the second station 62b, is conveyed to the third station 62c by the conveying plate 64. The cover glass 16, which has been taken out, by the holding-and-adhering means shown in FIG. 10, from the holder container 84 and mounted onto the mounting medium pattern 14. The action is controlled by the control section 3, which controls the motors 87 and 89.

The action of the holding-and-adhering means shown in FIG. 10 will be explained with reference to FIGS. 14A–14C.

Figure 14A:
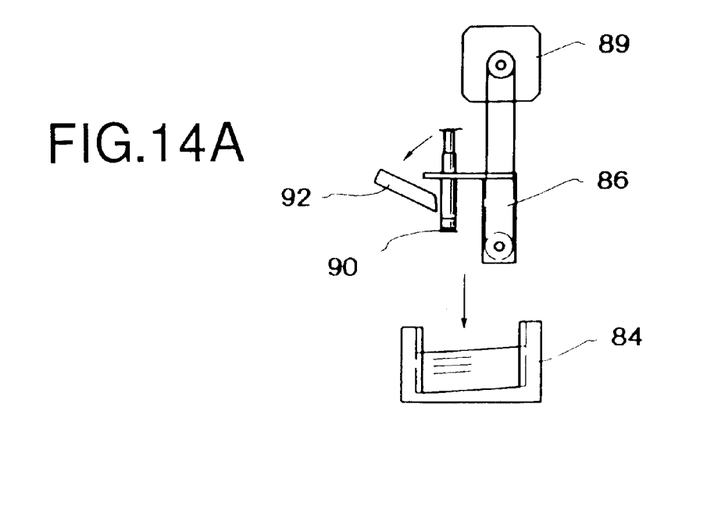
FIGS. 14A–14C are explanation views showing a series of action of taking out the cover glass by the holding-and-adhering means shown in FIG. 10.
Figure 14B:
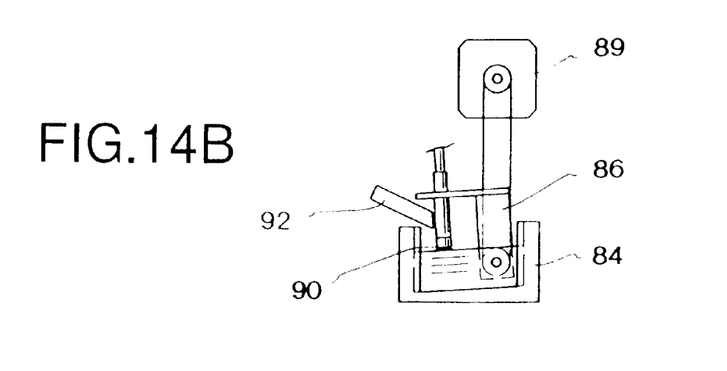

The arm 86, whose one end holds the sucking pad 90, is moved downward by the motor 89 so as to move the sucking pad 90 and the pin 92 toward the cover glasses piled in the holder container 84 (see FIG. 14A). The sucking pad 90 sucks and holds one end (lower end) of the uppermost cover glass 16a of the piled cover glasses 16, which have been slantingly piled in the holder container (see FIG. 14B). A front end of the pin 92, which is moved downward together with the sucking pad 90, is located above the sucking pad 90 holding the cover glass 16a.

Figure 14C:
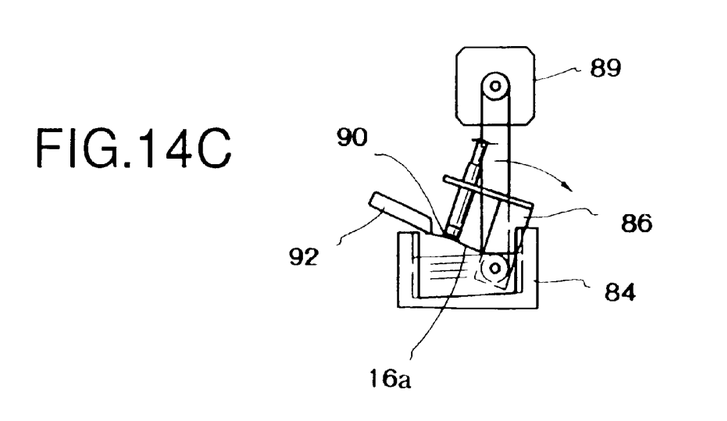

Next, the arm 86 is turned by the motor 87 (see FIG. 10) to make the other end of the uppermost cover glass 16a contact an inner face of the holder container 84 and bend the uppermost cover glass 16a (see FIG. 14C). The one end of the bent cover glass 16a is pressed downward by the pin 92, so that the cover glass 16a is deformed into an S-shape. It is difficult for a long cover glass to peel off from the piled cover glasses by merely bending, but the long cover glass can be easily peeled off by deforming into the S-shape. In the case of using short cover glasses which can be peeled off by merely bending, the pin 92 need not contact the one end of the cover glass.

The one end of the cover glass 16a, which is taken out from the holder container 84, is slantingly held by the sucking pad 90. Then the arm 86 is turned by the motors 87 and 89, so that the other end of the cover glass 16a contacts the upper face of the slide glass 12, which has been mounted on the third station 62c of the supporting member 62, and the one end of the cover glass 16a is gradually moved close to the upper face of the slide glass 12 (see FIG. 15). Moving speed of the arm 86 can be controlled by adjusting rotational speed of the motor 87. The rotational speed may be adjusted by the dial 32 of the operating panel 24 (see FIG. 2).

Figure 15:
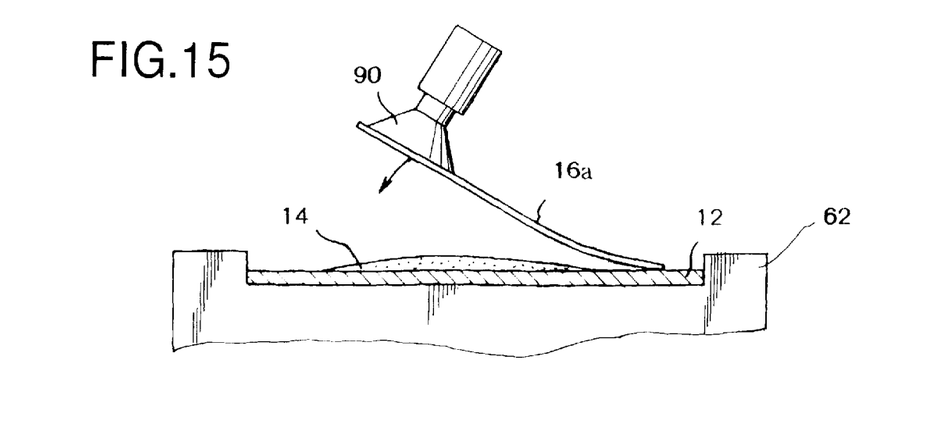
FIG. 15 is an explanation view showing action of mounting the cover glass onto the slide glass by the holding-and-adhering means shown in FIG. 10.

After the other end of the cover glass 16a contacts the slide glass 12, the moving speed of the arm 86 may be gradually changed, on the basis of characteristics of the mounting medium, speed of dropping the mounting medium, etc., by changing the rotational speed of the motor 87 so as to securely discharge air from the space between the cover glass 16a and the slide glass 12.

After mounting the cover glass 16a on the slide glass 12, the drop action of the drop nozzle 72 is stopped until the next slide glass 12 is prepared. In this case, the solvent in the mounting medium volatilizes, so that the mounting medium in the drop nozzle 72 is apt to solidify and close the drop nozzle 72. To avoid the solidification, in the dropping means shown in FIGS. 7 and 8, the control section 2 enters the lower end of the drop nozzle 72 into the container 80, which is located outside of the slide glass 12 and within the moving range of the drop nozzle 72 and in which the solvent is reservoired (see FIG. 16). If the drop action is stopped for a short time, the lower end of the drop nozzle 72 may be located in an air space between an entrance of the container 80 and solvent surface so as to prevent the solidification of the mounting medium in the drop nozzle 72. The air space is solvent environment.

Figure 16:
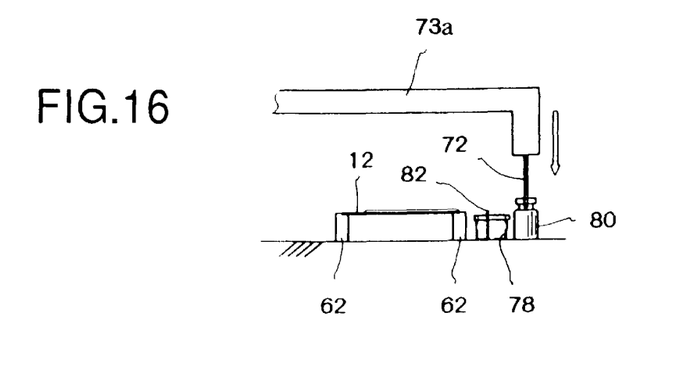
FIG. 16 is an explanation view showing action of entering a front end of a drop nozzle into a container of solvent, which is located outside of the slide glass and within a moving range of the drop nozzle.

On the other hand, if the drop action is stopped for a long time, e.g., one week or more, the lower end of the drop nozzle 72 should be dipped in the solvent.

If the drop nozzle is left in the air while the drop action is stopped, the mounting medium is apt to solidify. Conventionally, the drop nozzle is manually dipped into the solvent, but this work is troublesome for operators.

In the dropping means shown in FIGS. 7 and 8, the lower end of the drop nozzle 72 can be automatically entered the solvent container 80.

Conventionally, even if the drop action is stopped for a short time, the lower end of the drop nozzle is manually dipped into the solvent. So, the solvent in the drop nozzle must be replaced by the mounting medium when the drop action is restarted.

In the dropping means shown in FIGS. 7 and 8, if the drop action is stopped for a short time, the lower end of the drop nozzle 72 is located in the air space between the entrance of the container 80 and the solvent surface so as to prevent the solidification of the mounting medium in the drop nozzle 72. Namely, the replacement, which is required in the conventional drop means, is not required, so that useless cost can be removed and working efficiency can be improved.

In the embodiment shown in FIGS. 1–16, the cover glass adhering device is controlled by the three control sections 1, 2 and 3. The cover glass adhering device of the present invention may be controlled by one control section.

By using the cover glass adhering device of the present invention, fixed amount of the mounting medium can be always supplied to the slide glasses, the cover glasses having various length can be employed, the device can be small in size, and many microscope specimens can be automatically made for a short time. The cover glass adhering device of the present invention may be properly used in hospitals, etc.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. A cover glass adhering device, which mounts a cover glass onto a liquid mounting medium covering a microscope specimen on a respective slide glass of a plurality of slide glasses, comprising:
   a drop nozzle for dropping the mounting medium onto the specimen on a slide glass, which is held horizontally;
   a vertically extending removing member being located outside of the slide glasses, having a front end which contacts a drop of the mounting medium dangling from said drop nozzle and removes the drop therefrom so as to make dispersion of amounts of the drops dropped onto the slide glass as small as possible; and
   a traveling unit for traveling said drop nozzle, from which the dangling drop of the mounting medium has been removed by said removing member, along the slide glass so as to drop the prescribed amount of the mounting medium over the specimen.

2. The cover glass adhering device according to claim 1, wherein said traveling unit includes:
   an elevating unit for moving said drop nozzle in the vertical direction; and
   a sliding unit for sliding said drop nozzle along the specimen on the slide glass until a position outside of the slide glass.

3. The cover glass adhering device according to claim 1, further comprising a container, in which a solvent for preventing solidification of the mounting medium is reservoired, being located at a position, which is outside of the slide glass and at which a front end of said drop nozzle can enter said container.

4. The cover glass adhering device according to claim 1, further comprising a control section for controlling the movement of said traveling unit so as to put the front end of said drop nozzle into a container, in which a solvent for preventing solidification of the mounting medium is reservoired, before dropping the mounting medium, while stopping or after the dropping action.

5. The cover glass adhering device according to claim 1, further comprising:
   a holding member being capable of holding one end of an uppermost glass of the cover glasses, which have been slantingly piled in a holder container;
   a rotary unit for upwardly turning said holding member so as to downwardly bend the uppermost glass and remove the same from the adjacent cover glass; and
   a vertical drive unit for vertically moving said holding member and said rotary unit.

6. The cover glass adhering device according to claim 5, further comprising a pin being provided in the vicinity of said holding member, said pin downwardly pushing the uppermost cover glass, which is downwardly bent, so as to deform the uppermost cover glass into an S-shape.

7. The cover glass adhering device according to claim 1, further comprising:
   means for conveying a slide glass, said conveying means being provided between a basket container, in which a plurality of slide glasses, on each of which a microscope specimen is mounted, are accommodated, and a rack, in which the slide glasses, on each of which a cover glass is mounted to cover the specimen, will be accommodated, said conveying means having a conveyor plate, which intermittently conveys the slide glass, which is horizontally held, toward the rack;
   means for taking out the slide glass from the basket container and horizontally putting the slide glass onto a predetermined position in the conveyor plate; means for dropping a mounting medium, said dropping means including:
      the drop nozzle dropping the mounting medium onto the specimen on the slide glass, which has been horizontally conveyed to a predetermined position by said conveying means;
      the traveling unit for traveling said drop nozzle along the specimen on the slide glass so as to drop a prescribed amount of the mounting medium supplied by a supply unit, which is capable of supplying the prescribed amount of the mounting medium over the specimen; and
      a control section for controlling said traveling unit and said supply unit so as to stop the movement of said drop nozzle at a start end, at which said drop nozzle starts to drop the mounting medium onto the slide glass and move said drop nozzle along the slide glass after starting the drop action; and
   means for holding and adhering the cover glass, said holding-and-adhering means including:
      a holding member being capable of holding one end of an uppermost glass of the cover glasses, which have been slantingly piled in a holder container;
      a take-out unit turning said holding member so as to downwardly bend the uppermost glass and remove the same from the adjacent cover glass, then taking out the uppermost glass from the holder container; and
      a mounting unit gradually mounting the cover glass, whose one end is held by the holding member, onto the mounting medium, which covers the specimen on the slide glass conveyed to a predetermined position, from the other end to the one end.

8. The cover glass adhering device according to claim 7, wherein a supporting section of the rack, in which the slide glasses are accommodated, has a inclined face, with which side faces of the slide glasses come into contact.

9. The cover glass adhering device according to claim 7, wherein when the drop action of the drop nozzle moving along the surface of the slide glass is stopped, the movement of the drop nozzle is further continued until reaching the stop end after the drop action is stopped, so that the pattern of the mounting medium can be narrower toward the stop end.

10. The cover glass adhering device according to claim 7, wherein said traveling unit includes:
an elevating unit for moving said drop nozzle in the vertical direction; and
a sliding unit for sliding said drop nozzle along the specimen on the slide glass until a position outside of the slide glass.

11. The cover glass adhering device according to claim 7, further comprising a container, in which a solvent for preventing solidification of the mounting medium is reservoired, being located at a position, which is outside of the slide glass and at which a front end of said drop nozzle can enter said container.

12. The cover glass adhering device according to claim 7, wherein the control section of said dropping means controls the movement of said traveling unit so as to put the front end of said drop nozzle into a container, in which a solvent for preventing solidification of the mounting medium is reservoired, before dropping the mounting medium, while stopping or after the dropping action.

13. The cover glass adhering device according to claim 7, wherein said holding-and-adhering means comprises:
a sucking member being capable of sucking the one end of the uppermost glass of the cover glasses, which have been slantingly piled in the holder container;
a rotary unit for turning said sucking member so as to make the other end of the uppermost glass contact with an inner face of the holder container and bend the uppermost glass; and
a pin being provided in the vicinity of said sucking member, said pin downwardly pushing the uppermost glass, which is bent, so as to deform the uppermost cover glass into an S-shape.

14. The cover glass adhering device according to claim 1, further comprising:
a holder container for holding the stack of cover glasses on a slant, the holder container having an end wall engaging lower ends of the cover glasses;
a holding member for moving to and adhering to the cover glass disposed on top of the stack;
a rotary unit for turning said holding member so as to push the lower end of the cover glass against the end wall and downwardly bend the cover glass, and remove the cover glass from an adjacent cover glass of the stack;
a deforming member provided in a vicinity of said holding member, said deforming member downwardly pushing an end of the cover glass, which is downwardly bent, so as to deform the cover glass into an S-shape; and
a vertical drive unit for vertically moving said holding member and said rotary unit.

15. The cover glass adhering device according to claim 1, further comprising:
a holder container for holding the stack of cover glasses on a slant, the holder container having an end wall engaging lower ends of the cover glasses;
a holding member for moving to and adhering to the cover glass disposed on top of the stack;
a rotary unit for turning said holding member so as to push the lower end of the cover glass against the end wall and downwardly bend the cover glass, and remove the cover glass from an adjacent cover glass of the stack; and
a vertical drive unit for vertically moving said holding member and said rotary unit.

16. The cover glass adhering device according to claim 15, further comprising:
a control section for controlling said traveling unit so as to stop the movement of said drop nozzle at a start end, at which said drop nozzle starts to drop the mounting medium onto the slide glass and move said drop nozzle along the slide glass after starting the drop action.

17. The cover glass adhering device according to claim 15, further comprising:
a deforming member provided in a vicinity of said holding member, said deforming member downwardly pushing an end of the cover glass, which is downwardly bent, so as to deform the cover glass into an S-shape.

18. The cover glass adhering device according to claim 1, further comprising a constant amount liquid supplying unit for supplying the mounting medium to said drop nozzle.

19. The cover glass adhering device according to claim 18, wherein said constant amount liquid supplying unit is a plunger pump.

20. The cover glass adhering device according to claim 1, wherein said vertically extended removing member is a plate.

21. The cover glass adhering device according to claim 1, wherein said vertically extended removing member has a vertical dimension and a horizontal dimension and said vertical dimension is greater than said horizontal dimension.

22. A cover glass adhering device, which mounts a cover glass onto a liquid mounting medium covering a microscope specimen on a respective slide glass of a plurality of slide glasses, comprising:
a drop nozzle for dropping the mounting medium onto the specimen on a slide glass, which is held horizontally;
a traveling unit for traveling said drop nozzle in a prescribed direction;
a container located outside of the slide glasses, said container storing a solvent which prevents solidification of the mounting medium; and
a control unit inserting a front end of said nozzle into a solvent atmosphere, which is produced in said container, so as to prevent the solidification of the mounting medium left in the front end of said drop nozzle when dropping the mounting medium is once stopped, said control unit controlling said traveling unit so as to travel said drop nozzle along the slide glass so that said drop nozzle drops the mounting medium over the specimen.

23. The cover glass adhering device according to claim 22, wherein the solvent atmosphere is produced in a space between an inlet of said container and a liquid surface of the solvent therein.

24. The cover glass adhering device according to claim 23, wherein said control unit inserts the front end of said nozzle into the space between the inlet of said container and the liquid surface of the solvent when dropping the mounting medium is once stopped.

25. The cover glass adhering device according to claim 22, further comprising a constant amount liquid supplying unit for supplying the mounting medium to said drop nozzle, wherein said control unit controls said traveling unit and said liquid supplying unit so as to move said drop nozzle along the slide glass and drop a mount of the mounting medium over the specimen.

26. The cover glass adhering device according to claim 25, wherein said liquid supplying unit is a plunger pump.

* * * * *